United States Patent
Lee

(10) Patent No.: US 10,363,205 B2
(45) Date of Patent: Jul. 30, 2019

(54) DELAYED RELEASE DELIVERY SYSTEMS AND METHODS

(71) Applicant: ELC MANAGEMENT LLC, Melville, NY (US)

(72) Inventor: Wilson A. Lee, Hauppauge, NY (US)

(73) Assignee: ELC MANAGEMENT LLC, Melville, NY (US)

( * ) Notice: Subject to any disclaimer, the term of this patent is extended or adjusted under 35 U.S.C. 154(b) by 0 days.

(21) Appl. No.: 15/712,431

(22) Filed: Sep. 22, 2017

(65) Prior Publication Data

US 2018/0110687 A1    Apr. 26, 2018

Related U.S. Application Data

(60) Provisional application No. 62/413,227, filed on Oct. 26, 2016.

(51) Int. Cl.

| | | |
|---|---|---|
| A61K 8/02 | (2006.01) | |
| A61K 8/11 | (2006.01) | |
| A61K 8/58 | (2006.01) | |
| A61K 8/06 | (2006.01) | |
| A61K 8/34 | (2006.01) | |
| A61Q 5/00 | (2006.01) | |
| A61Q 19/00 | (2006.01) | |
| A61Q 13/00 | (2006.01) | |
| A61K 8/894 | (2006.01) | |

(52) U.S. Cl.
CPC .............. *A61K 8/0279* (2013.01); *A61K 8/06* (2013.01); *A61K 8/11* (2013.01); *A61K 8/345* (2013.01); *A61K 8/585* (2013.01); *A61K 8/894* (2013.01); *A61Q 5/00* (2013.01); *A61Q 13/00* (2013.01); *A61Q 19/00* (2013.01); *A61K 2800/412* (2013.01); *A61K 2800/623* (2013.01); *A61K 2800/624* (2013.01); *A61K 2800/652* (2013.01)

(58) Field of Classification Search
CPC .................................. A61K 8/11; A61K 8/0279
See application file for complete search history.

(56) References Cited

U.S. PATENT DOCUMENTS

| | | | |
|---|---|---|---|
| 4,020,156 A | 4/1977 | Murray et al. | |
| 4,438,016 A | 3/1984 | Kiewert et al. | |
| 4,579,717 A | 4/1986 | Gyulay | |
| 4,954,285 A | 9/1990 | Wierenga et al. | |
| 5,041,421 A | 8/1991 | King | |
| 5,246,919 A | 9/1993 | King | |
| 5,336,665 A | 8/1994 | Garner-Gray et al. | |
| 6,245,733 B1 | 6/2001 | Mosbaugh | |
| 6,769,271 B2 | 8/2004 | Mosbaugh | |
| 7,294,612 B2 | 11/2007 | Popplewell et al. | |
| 7,399,324 B2 | 7/2008 | Roddenbery et al. | |
| 7,622,132 B2 | 11/2009 | Lee et al. | |
| 7,655,744 B2 | 2/2010 | Miyanaga | |
| 7,833,960 B2 | 11/2010 | Lei et al. | |
| 8,246,997 B2 | 8/2012 | Lee | |
| 8,921,303 B1 | 12/2014 | Lull et al. | |
| 8,932,564 B2 | 1/2015 | Lee | |
| 8,932,639 B2 | 1/2015 | Lee | |
| 2005/0074474 A1 * | 4/2005 | Sako ........................ A61K 8/25 424/401 |
| 2005/0112152 A1 | 5/2005 | Popplewell et al. | |
| 2005/0233074 A1 | 10/2005 | Dalziel et al. | |
| 2006/0153889 A1 | 7/2006 | Friel et al. | |
| 2006/0165740 A1 | 7/2006 | Frank | |
| 2009/0304756 A1 | 12/2009 | Dahne et al. | |
| 2011/0014298 A1 | 1/2011 | Friel et al. | |
| 2011/0269657 A1 | 11/2011 | Dihora et al. | |

FOREIGN PATENT DOCUMENTS

| | | |
|---|---|---|
| CA | 2730716 | 2/2010 |
| CN | 105753368 | 7/2016 |
| EP | 0332259 | 9/1989 |
| EP | 0492007 | 7/1992 |
| GB | 864919 | 4/1961 |
| JP | H0382471 | 4/1991 |
| JP | H10179707 | 7/1998 |
| JP | 2009012996 | 1/2009 |

OTHER PUBLICATIONS

Cabot; Cab-O-Sil Fumed Metal Oxides for Coatings; Fumed Metal Oxides; Selection Guide ; 3 pages.
Florite; Tomita Pharmaceutical Co., Ltd.; 4 pages.
htpp://www.kruss.de/prducts/tensiometers/k100/force-tensiometer-k100; Force Tensiometer—K100; pp. 1-4.
http://ww.ulprospector.com/en/eu/Personal/Care/Detail/4728/238202/ FLORITE-R; Prospector; Florite R; Florite R by Kobo Products, Inc.—Personal Care & Cosmetics; Sep. 2016.
http://www.ulprospector.com/en/eu/Personal/CareDetail/4034/361102/ Gransil-VX-418; Prospector; Gransil VX-418; Gransil VX-418 by Grant Industries, Inc.—Personal Care & Cosmetics; Oct. 2016.
http://www.ulprospector.com/en/na/Personal/Care/Detail/259/375468/ Dow-Corning-2501-Cosmetic Wax; Prospector; Dow Corning 2501 Cosmetic Wax; Dow Corning 2501 Cosmetic Wax by Dow Corning Corporation—Personal Care & Cosmetics; Oct. 2016.
PCT International Search Report; International Application No. PCT/US2017/052916; Completion Date: Dec. 20, 2017; dated Dec. 20, 2017.
PCT International Search Report; International Application No. PCT/US2017/052933; Completion Date: Dec. 20, 2017; dated Dec. 20, 2017.

(Continued)

*Primary Examiner* — Kyle A Purdy
(74) *Attorney, Agent, or Firm* — Cynthia Miller; Tiffany A. Johnson

(57) ABSTRACT

A delayed release delivery system comprises a hydrophilic core particle having surface pores and containing a liquid. The particle is encapsulated in a polymer having a hydrophobic backbone and hydrophilic pendant groups. At least some of the surface pores adjacent the hydrophilic pendant groups are blocked in the presence of water and unblocked in the absence of water. The treated particle contains liquid in a weight ratio of the liquid to the porous core particle of at least 400:1.

9 Claims, No Drawings

(56) References Cited

OTHER PUBLICATIONS

PCT International Search Report; International Application No. PCT/US2017/052939; Completion Date: Dec. 20, 2017; dated Dec. 20, 2017.
PCT International Search Report; International Application No. PCT/US2017/052946; Completion Date: Jan. 2, 2018; dated Jan. 3, 2018.
PCT Written Opinion of the International Searching Authority; International Application No. PCT/US2017/052916 Completion Date: Dec. 20, 2017; dated Dec. 20, 2017.
PCT Written Opinion of the International Searching Authority; International Application No. PCT/US2017/052933 Completion Date: Dec. 20, 2017; dated Dec. 20, 2017.
PCT Written Opinion of the International Searching Authority; International Application No. PCT/US2017/052939 Completion Date: Dec. 20, 2017; dated Dec. 20, 2017.
PCT Written Opinion of the International Searching Authority; International Application No. PCT/US2017/052946 Completion Date: Jan. 2, 2018; dated Jan. 3, 2018.
www.koboproducts.com; Microspheres; Technical Literature ref MSp-003; pp. 1-2; Jul. 2016.

* cited by examiner

DELAYED RELEASE DELIVERY SYSTEMS AND METHODS

FIELD OF THE INVENTION

The present invention relates to particles which can act as a sustained delivery system for fragrance or skin, scalp and hair benefit ingredients, methods for preparing the particles, and compositions containing the particles. More specifically, the particles absorb fragrance or actives and release the fragrance or actives gradually over an extended period of time.

BACKGROUND OF THE INVENTION

Fragrance is used in a variety of products to enhance the consumer's delight in using those products. The desirability of producing products which retain their scent for an extended period of time after application to skin, scalp or hair, has long been recognized. Despite many efforts in this direction, most commercial products for skin, scalp and hair have an intense, pleasant odor initially but, disappointingly, tend to lose their scents within minutes after being applied. Attempts made to solve the problem include using inorganic carriers impregnated with fragrance for incorporation into products. EP 0 332 259A discloses perfume particles made by adsorbing perfume onto silica. U.S. Pat. No. 5,336,665 discloses free-flowing hydrophobic porous inorganic hydrophobic carrier particles, such as aluminosilicates, having a certain pore volume and pore diameter and having perfume adsorbed into the particles. A fragrant material composed of aggregates of sodium chloride granules and having a fragrant oil absorbed in the pores between granules is disclosed in U.S. Pat. No. 5,246,919.

Efforts have been made to increase the amount of time that fragrances remain on keratinous surfaces of the body without increasing fragrance load, such as by the use of coatings and microencapsulation systems. A fragrant bead composition made up of a multiplicity of prilled urea beads having an adherent surface coating containing a fragrance is described in U.S. Pat. No. 4,020,156. A discontinuous surface coating for particles which permits a controlled release of actives from an underlying deposit on a core particle is described in U.S. 2006/0153889.

Microencapsulation technology is well known in the art and is generally directed to encapsulating core materials that require protection until time of use in a protective covering. Generally, a high viscosity fluid will be dispersed more slowly from a carrier which tends to extend fragrance duration, while a lower viscosity fluid will enhance the intensity of the scent by virtue of a higher evaporation rate. Time release microcapsules release their core materials at a controlled rate. The result is that the encapsulated material has a longer effective life since it is not immediately released from the protective microcapsule. A polymeric encapsulated liquid fragrance which is further treated with a cationic polymer to improve deposition is described in U.S. Pat. No. 7,294,612. A pre-glass agglomeration of fused microspheres uses microcapillary action to quickly uptake oil-based or alcohol-based liquids to more than double the weight of the pre-glass agglomeration, as described in U.S. Pat. No. 6,245,733. A cosmetic material encapsulated by a frangible capsule of thermo-softening material that is solid at room temperature but which will rupture when the composition is rubbed on a skin surface and melts up on application to the skin is described in U.S. Pat. No. 7,622,132.

Notwithstanding the above, there is still an ongoing need for fragranced products which demonstrate an extended duration of continuous release of fragrance to the skin, scalp and hair, over extended periods of time.

SUMMARY OF THE INVENTION

According to one aspect of the invention, a delayed release delivery system comprising at least one treated particle is provided.

In one embodiment of this aspect of the invention, the treated particle comprises a hydrophilic core particle having surface pores and a liquid contained therein. The hydrophilic core particle is further encapsulated by a polymer having a hydrophobic backbone and a plurality of hydrophilic pendant groups. At least some of the surface pores adjacent the hydrophilic pendant groups are blocked in the presence of water and unblocked in the absence of water.

In a further embodiment of this aspect of the invention, the treated particle comprises a porous core particle having a porous surface, and a liquid absorbed therein. The weight ratio of the liquid to the porous core particle is at least about 400:1, such as from about 400:1 to about 800:1.

In accordance with a further aspect of the invention, a method for preparing a delayed release delivery system is provided.

In one embodiment of this aspect of the invention, the method for preparing a delayed release delivery system includes the steps of:

(a) providing at least one hydrophilic core particle having surface pores and having a liquid absorbed therein;

(b) contacting the particle of (a) with a liquid polymer for a time sufficient to encapsulate the at least one particle with the liquid polymer to form at least one treated particle, wherein the liquid polymer has a hydrophobic backbone and a plurality of hydrophilic side chains, and wherein at least some of the surface pores on the hydrophilic core particle adjacent the hydrophilic side chains are blocked in the presence of water and unblocked in the absence of water; and (c) dispersing the at least one treated particle in an aqueous-containing cosmetically acceptable vehicle.

In accordance with a further embodiment of this aspect of the invention, the method for preparing a delayed release delivery system comprises the steps of:

(a) providing a porous core particle; and (b) contacting the porous core particle with a liquid under conditions sufficient for the liquid to be absorbed into the core particle in the weight ratio of the liquid to the porous core particle of at least about 400:1.

DETAILED DESCRIPTION OF THE PREFERRED EMBODIMENTS OF THE INVENTION

Delayed release delivery systems of the invention comprise a porous particle having a liquid absorbed therein.

A delayed release delivery system comprises at least one treated particle comprising a hydrophilic core particle having surface pores which is encapsulated with a polymer. The polymer has a hydrophobic backbone and a plurality of hydrophilic pendant groups. The polymer blocks pores on the surface of the treated particle with the exception that at least some pores on the particle surface which are situated adjacent the hydrophilic pendant groups on the polymer are blocked in the presence of water and unblocked in the absence of water. In the presence of an aqueous-containing environment, a liquid contained within the treated particle is retained in the particle, since water molecules are attracted to the hydrophilic pendant groups and block at least some of the surface pores adjacent the pendant groups.

The treated particles maintain integrity when suspended in an aqueous-containing base during storage, or in an aqueous-containing product. Upon being rubbed into skin, for example, as the water in the product evaporates, the water molecules blocking pores adjacent the hydrophilic pendant groups on the polymer pull away from the pores permitting a liquid contained in the treated particle to be gradually released through the pores in a slow and sustained manner.

Any hydrophilic porous core particle capable of absorbing liquid may be used in preparing the delayed release delivery system. Typically, such particles are formed of an inorganic material, including, but not limited to silica, silica silylate, and calcium silicate. Microspheres formed of these inorganic materials, and particularly, hydrophilic microspheres, are preferred for use in the delayed release delivery systems of the invention. Hydrophilic microspheres useful in the invention may be natural or synthetic and have an average particle size of from about 100 nm to about 50 µm. Microspheres having a high affinity for oil absorption are particularly preferred. One such microsphere is formed of calcium silicate, available as Florite® from Tomita Pharmaceutical Co., Ltd., having a particle size of about 29 µM. This synthetic material has a petaloid crystal structure with notably deep, large pore size and volume, and excellent liquid absorbency. In comparison with other inorganic materials, this calcium silicate absorbs oil and water of at least five times its weight. 650 g of oil are absorbed by 100 g of this calcium silicate powder. Microspheres formed from silica, such as Silica shells Jr. are also useful. These microspheres, available from KOBO, have a particle size of about 3 µM and absorb 400-600 g of oil per 100 g of silica powder. Also useful are microspheres formed of silica silylate, a fumed silica, available as CAB-O-SIL TS-530 from Cabot. The silica is treated with hexamethyldisilazane. The treatment replaces many of the surface hydroxyl groups with trimethylsilyl groups rendering the silica extremely hydrophobic.

Polymers useful in the delayed delivery systems of the present invention have a hydrophobic backbone and pendant hydrophilic groups or side chains. The backbone of the polymer is sufficiently hydrophobic to adhere well to the surface of the liquid-filled porous particle. The hydrophilic side chains behave like the bristles of a brush. They are sufficiently long and suitably spaced along the polymer backbone to enable the side chains to not only attract water but to trap and hold it. Particularly preferred polymers are those having a silicone backbone. Silicone adheres well to the porous particles and may be modified by the addition of hydrophilic side chains. One such preferred polymer has a silicone backbone with polyglycerol side chains. The silicone backbone or hydrophobic side of the polymer adheres to the porous particle surface, anchoring in the pores. This polymer adheres particularly well to hydrophilic porous particles filled with an oil-containing liquid. Oil in the pores makes the hydrophilic particle behave like a hydrophobic particle so as to enable the polymer to adhere well to the particle surface. The polyglycerol side chains form the hydrophilic side of the polymer and do not attach to the microsphere surface. When polymer-coated treated particles of the invention are dispersed in an aqueous-containing base, water molecules in the base are attracted to the side chains. The water molecules hydrogen bond to the side chains and surround each particle. The water molecules plug the spaces in the polymer at the points where the side chains extend from the polymer backbone. The greater the number of the side chains, the more water is associated with the treated particles. When an aqueous-containing product containing the treated particles is rubbed into skin, water evaporates from the product containing the treated particles. The water associated with the treated particles is the last to evaporate. Once those water molecules are no longer available to plug the holes in the silicone backbone (where the side chains are located), the previously plugged pores in those areas are exposed, and fragrance begins to exit the treated particle.

Ambient humidity levels can affect evaporation of water from the product containing the liquid-filled treated particles. The higher the ambient humidity, the slower the release of liquid due to slower evaporation of water.

The more liquid entrapped in the treated particles, the longer it will take for the liquid, for example, a fragrance oil-containing liquid, to be released and the longer the duration of the scent on the skin. The diffusivity of the liquid will also affect the release time.

Suspending the treated particles in a non-compatible vehicle can further retard the release of the liquid entrapped in the particle pores. For example, a treated particle containing a fragrance oil may be dispersed in an aqueous base for storage, or in an aqueous-containing product.

Another factor which would be expected to impact controlled release of the liquid, for example a fragrance oil, and therefore the endurance of fragrance on the skin, includes the thickness of the polymer coating on the porous particles. As the polymer coating is hydrophobic, once water has evaporated from a skin product, oil on the skin will slowly dissolve the coating on the treated particles, permitting the liquid to escape. As polymer thickness increases, the longer will be the duration of the release of the entrapped liquid.

Similarly, the amount of the oil phase in a product in which the treated particles are incorporated will also have an effect on the timed release of contained liquid. Once water has evaporated from the product, the oil in the product will begin to gradually dissolve the hydrophobic polymer coating and lead to the sustained release of the liquid from the particles. The lesser the amount of the oil phase in the product, the slower the release of the liquid.

The amount of liquid-containing treated particles in a product containing the particles will also impact the duration of fragrance on the skin to which the product is applied.

Any liquid capable of being absorbed into the hydrophilic core particles may be used in preparing the delayed release delivery system. The liquid may be aqueous-based, oil-based, an oil-in-water emulsion, a silicone-in-water emulsion, a water-in-oil emulsion, a water-in-silicone emulsion, or a multiple emulsion. Preferably, the liquid will be selected from those containing a fragrance oil, a skin, scalp or hair benefit active, and combinations thereof.

The delayed release delivery system may be prepared by the following steps:

(a) providing at least one hydrophilic core particle having surface pores and a liquid absorbed therein;

(b) contacting the particle of (a) with a liquid polymer under conditions sufficient to encapsulate the at least one particle with the liquid polymer to form at least one treated particle, wherein the liquid polymer has a hydrophobic backbone and a plurality of hydrophilic side chains, and wherein at least some of the surface pores on the hydrophilic core particle adjacent the hydrophilic side chains are blocked in the presence of water and unblocked in the absence of water; and (c) dispersing the at least one treated particle in an aqueous-containing cosmetically acceptable vehicle.

The hydrophilic core particle may be any hydrophilic porous particle capable of absorbing liquid therein, as discussed hereinabove.

Any liquid capable of being absorbed into the hydrophilic core particles may be used in preparing the delayed release delivery system, as discussed hereinabove. The liquid may be absorbed into the at least one hydrophilic core particle by any suitable method known in the art.

The step of contacting the liquid-filled treated particle with the polymer may be carried out using any suitable method known to those skilled in the art for applying a coating to a particle, including, but not limited to, at least one of mixing, spray coating, and sonication.

A preferred method of encapsulating the liquid-filled core particles with the polymer is by the use of sonication. The average size of the liquid-filled particles (e.g., 3 μm silica particles filled with a fragrance oil-containing liquid) is measured by Transmission Electronic Microscopy (TEM). 70% water, 28% liquid-filled particles and 2% liquid polymer are mixed in a vessel to form a slurry. The slurry is then sonicated for 30 minutes with medium intensity, 20 kHz, at 25° C. using an ultrasonic probe such as available from Sonicor Instrument Co., to result in a thick colloidal suspension. The suspension is centrifuged for 15 minutes at 1000 rpm in order to precipitate the particles and remove unattached polymer material. The resultant mixture is washed with deionized water, and the washing procedure is repeated three times. TEM is used again after sonication to measure the uniformity and the thickness of the polymer coating on the treated particles. The thickness of the polymer coating will be that amount which will permit the polymer to anchor to the pores, while avoiding a too thick coating which may be expected to adversely affect the release of the liquid. The polymer thickness will preferably be in the range of from about 10 nm to about 30 nm. A coating of less than about 10 nm would not be expected to uniformly coat the porous particle, while a thickness of greater than about 30 nm may be expected to essentially prevent the release of the liquid from the treated porous particles. To prevent dehydration of the treated particles, which would activate the release of the liquid, the treated particles are then submerged in about 70 weight % water.

Polymers suitable for use in the delayed release delivery system of the invention include, but are not limited to, any of those discussed hereinabove.

In a further embodiment of the present invention, the delayed delivery system comprises at least one treated particle comprising a core particle having a porous surface, and a liquid absorbed in the core particle. The ratio of the weight of the liquid to the weight of the core particle being at least about 400:1. More preferably, the ratio is between about 400:1 and about 800:1, including any ratio therebetween, including 401:1 to 799:1, and any range therein.

Any porous particle capable of absorbing liquid may be used in preparing the delayed release delivery system, as discussed hereinabove.

The delayed release delivery system may be prepared by the following steps:

(a) providing a porous core particle; and (b) contacting the porous core particle with the liquid under conditions sufficient for the liquid to be absorbed into the porous core particle in the weight ratio of the liquid to the porous core particle of at least about 400:1.

Porous core particles useful in this method for preparing the delayed release delivery system may include any porous particle capable of absorbing liquid therein. Useful porous particles may include, but are not limited to, the hydrophilic particles discussed hereinabove.

The liquid is absorbed into the core particle by contacting the core particle with the liquid at a pressure of at least 100 psi for at least 30 minutes. More preferably, the pressure used is in the range of greater than 100 psi to about 1000 psi, including any value there-between, including 101 to 999 psi and any integer within that range, such as 300 psi, 500 psi, 700 psi, and so forth, The contacting time may be any time from about 30 minutes up to about 2 hours, such as for about 1 hour. The contacting step may be repeated at least once, for example, one to three times. The high pressure spreads the pores in the particles enabling the particles to hold more liquid, and also propels the liquid into the pores. The pressure and the time needed to achieve the desired amount of liquid absorption increase proportionately with the density of the liquid. Generally, porous particles and the liquid to be absorbed are mixed in a ratio of from about 1:5 to about 1:10 of porous particles to liquid, and the resulting slurry is transferred to a high pressure tank. The slurry is then subjected to high pressure for at least 30 minutes, and up to about 2 hours.

The method may further comprise the step of encapsulating the treated particle in a polymer coating as described hereinabove.

The absorption of liquid by the porous core particle (e.g., microsphere) may be facilitated by compatibilizing the surface tension of the liquid with the surface tension of the porous particle. The surface tension of the liquid may be in the range of from about 30-72 dyne/cm. For example, a hydrophobic liquid, such as a liquid containing a fragrance oil, may have a surface tension in the range of from about 30-45 dyne/cm. Diluents may be combined to modify the surface tension of the fragrance oil. A porous particle containing a hydrophobic liquid, such as a fragrance oil, will typically have a surface tension in the range of from about 40-70 dyne/cm. The surface tension is modified in certain embodiments in which a polymer having a hydrophobic backbone and hydrophilic side chains or pendant groups is coated onto the liquid-containing porous particle. In that case, the surface tension of the coated particle will be in the range of from about 60-72 dyne/cm to ensure that the treated particles are dispersible in the water phase of a product. As discussed above, when water evaporates from the aqueous-containing product, release of the liquid contained in the porous particle will be activated. Surface tension may be measured by any method known in the art for this purpose. An example of an instrument useful in measuring surface tension of liquids is the Force Tensiometer—K100, available from Krüss.

One method for determining the pressure and time needed for a particular liquid, for example, a liquid containing a fragrance oil, to be absorbed into the porous particles, uses confocal laser scanning microscopy (CLSM). Samples are prepared by mixing fragrance oil with a fluorescent dye, for example, Nile red, incorporating the dye-containing oil into diluent, and mixing the liquid with core particles under conditions of varying pressure and time. Each prepared sample of the liquid-containing microspheres is placed on a micro slide and examined under the confocal microscope. Emitted/reflected light is transmitted to electrical signals by a photomultiplier and displayed on a computer monitor screen. This method permits measurement of the surface area and mathematical calculation of the volume occupied by the fragrance oil.

Any liquid capable of being absorbed into the core particles may be used in preparing the delayed release delivery system, as discussed hereinabove. Liquids, containing fragrance or actives in diluent, to be absorbed by the core particles, may be hydrophilic or hydrophobic. As discussed hereinabove, for optimal loading of liquid in the porous particle, the surface tensions of the liquid and the core particle should be compatible. For example, to modify the surface tension of a fragrance oil to be more compatible with the surface tension of the core particle the fragrance oil may be combined with one or more diluents.

Fragrances suitable for use in this invention include without limitation, any fragrance of combination of fragrances, including fragrant oils, plant extracts, synthetic fragrances, or mixtures thereof, which are compatible with and capable of being encapsulated in the delayed release delivery systems of the invention, and which also are compatible with the encapsulation processes employed. Suitable fragrances include but are not limited to those derived from fruits, flowers, and herbs, as well as oils, including essential oils. A source of suitable fragrances is found in *Poucher's Perfumes Cosmetics and Soaps*, Tenth Edition, Hilda Butler, 2000.

Treated particles, whether or not encapsulated in polymer, may be suspended in a cosmetically acceptable vehicle. Such cosmetically acceptable vehicle may be aqueous-based, oil-based, an oil-in-water emulsion, a silicone-in-water emulsion, a water-in-oil emulsion, a water-in-silicone emulsion, or a multiple emulsion. In the case of the treated particle encapsulated in polymer, the vehicle will be aqueous-containing. The vehicle may comprise a cosmetically further cosmetically acceptable skin, scalp or hair benefit ingredient.

What is claimed is:

1. A delayed release delivery system, comprising:
   at least one treated particle, the treated particle, comprising:
      a hydrophilic core particle having surface pores and a liquid contained therein, the hydrophilic core particle being further encapsulated by a polymer having a hydrophobic backbone and a plurality of hydrophilic pendant groups,
         wherein at least some of the surface pores adjacent the hydrophilic pendant groups are blocked in the presence of water and unblocked in the absence of water, and
         wherein the polymer is modified with polyglycerol pendant groups.

2. The delayed release delivery system of claim 1, wherein the polymer comprises a silicone backbone.

3. The delayed release delivery system of claim 1, wherein the liquid is aqueous-based, oil-based, an oil-in-water emulsion, a silicone-in-water emulsion, a water-in-oil emulsion, a water-in-silicone emulsion, or a multiple emulsion.

4. The delayed release delivery system of claim 1, wherein the liquid comprises a fragrance oil, a skin benefit active, a scalp benefit active, a hair benefit active, or a combination thereof.

5. The delayed release delivery system of claim 1, wherein the liquid and the treated particle have compatible surface tensions.

6. The delayed release delivery system of claim 1, wherein the hydrophilic core particle is a microsphere having an average particle size ranging from approximately 100 nm to approximately 50 μm.

7. The delayed release delivery system of claim 6, wherein the hydrophilic core particle is provided with a series of micropores extending from the surface of the particle through the core.

8. A cosmetic composition, comprising:
   the delayed release delivery system of claim 1 in an aqueous-containing cosmetically acceptable vehicle.

9. The cosmetic composition of claim 8, comprising:
   at least one further skin, scalp or hair benefit ingredient.

* * * * *